(12) United States Patent
Tanaka

(10) Patent No.: US 11,879,782 B2
(45) Date of Patent: Jan. 23, 2024

(54) EAR THERMOMETER

(71) Applicant: BIO ECHO NET INC., Sapporo (JP)

(72) Inventor: Hideki Tanaka, Sapporo (JP)

(73) Assignee: BIO ECHO NET INC., Sapporo (JP)

( * ) Notice: Subject to any disclaimer, the term of this patent is extended or adjusted under 35 U.S.C. 154(b) by 228 days.

(21) Appl. No.: 17/411,009

(22) Filed: Aug. 24, 2021

(65) Prior Publication Data

US 2021/0381898 A1    Dec. 9, 2021

Related U.S. Application Data

(63) Continuation of application No. PCT/JP2020/006654, filed on Feb. 20, 2020.

(30) Foreign Application Priority Data

Feb. 27, 2019  (JP) ................................ 2019-033609

(51) Int. Cl.
  *G01J 5/00* (2022.01)
  *G01J 5/04* (2006.01)
  *G01J 5/20* (2006.01)

(52) U.S. Cl.
  CPC ............. *G01J 5/0011* (2013.01); *G01J 5/049* (2013.01); *G01J 5/20* (2013.01)

(58) Field of Classification Search
  CPC .................................. G01J 5/0011; G01J 5/20
  See application file for complete search history.

(56) References Cited

U.S. PATENT DOCUMENTS

| 4,900,162 A | * | 2/1990 | Beckman | ................ | G01J 5/061 |
|  |  |  |  |  | 374/2 |
| 5,874,735 A | * | 2/1999 | Matsumoto | ............. | H01J 37/28 |
|  |  |  |  |  | 250/310 |

(Continued)

FOREIGN PATENT DOCUMENTS

| CN |  | 1391092 A | * | 1/2003 |
| CN |  | 201798735 U | * | 4/2011 |

(Continued)

OTHER PUBLICATIONS

International Search Report and Written Opinion (PCT/ISA/237) for PCT/JP2020/006654, dated Apr. 21, 2020 4 pages.

(Continued)

*Primary Examiner* — Gail Kaplan Verbitsky
(74) *Attorney, Agent, or Firm* — Procopio, Cory, Hargreaves & Savitch LLP

(57) ABSTRACT

An ear thermometer includes a probe including an infrared sensor unit for measuring a temperature of an eardrum of an ear of a temperature measurement target parson in a non-contact manner, the probe attached to an ear hole of the temperature measurement target parson. The probe includes a probe body inserted into the ear hole of the temperature measurement target parson, a housing for supporting the probe body; and an in-ear type earpiece attached to the probe body and abutting on an inside of the ear hole of the temperature measurement target person. The infrared sensor unit includes a first sensor and a second sensor arranged in the probe body and spaced apart by a predetermined distance along a direction substantially orthogonal to the eardrum when the probe body is inserted into the ear hole of the temperature measurement target person.

4 Claims, 5 Drawing Sheets

(56) References Cited

U.S. PATENT DOCUMENTS

| | | | |
|---|---|---|---|
| 6,435,711 B1 * | 8/2002 | Gerlitz | G01J 5/16 374/E13.003 |
| 10,816,412 B2 * | 10/2020 | Park | G01V 8/00 |
| 11,125,622 B2 * | 9/2021 | Marsh | G01J 5/0011 |
| 2002/0191670 A1 * | 12/2002 | Huang | G01J 5/049 600/549 |
| 2003/0016728 A1 | 1/2003 | Gerlitz et al. | |
| 2004/0057494 A1 * | 3/2004 | Tsao | G01J 5/10 374/E13.003 |
| 2004/0228386 A1 * | 11/2004 | Tabata | G01J 5/04 374/121 |
| 2007/0206657 A1 | 9/2007 | Lin et al. | |
| 2010/0183044 A1 | 7/2010 | Tanaka | |
| 2012/0257649 A1 | 10/2012 | Tanaka | |
| 2013/0296685 A1 | 11/2013 | Tsuboi et al. | |

FOREIGN PATENT DOCUMENTS

| | | | | |
|---|---|---|---|---|
| CN | 102058398 A | | 5/2011 | |
| EP | 2161556 A1 | | 3/2010 | |
| JP | H674102 U | * | 10/1994 | |
| JP | H11-281489 A | | 10/1999 | |
| JP | 2000-186963 A | | 7/2000 | |
| JP | 2005288190 A | | 10/2005 | |
| JP | 3134746 U | * | 8/2007 | |
| JP | H08191800 A | * | 7/2009 | |
| JP | 5039618 B | | 10/2012 | |
| JP | 2014194365 A | | 10/2014 | |
| TW | 200804777 A | | 5/2006 | |
| WO | WO-9522928 A1 | * | 8/1995 | G01J 5/02 |
| WO | WO-0016046 A2 | * | 3/2000 | G01J 5/02 |
| WO | WO-0196825 A1 | * | 12/2001 | G01J 5/02 |
| WO | WO-2021025038 A1 | * | 2/2021 | A61B 5/0245 |

OTHER PUBLICATIONS

International Search Report and Written Opinion (PCT/ISA/237) for PCT/JP2020/006654, dated Feb. 27, 2019. 4 pages.

Official Action for Taiwanese Application No. 109105470, dated Aug. 11, 2020, 5 pages.

European Patent Office, Extended European Search Report, Application No. 20763390.0-113, dated Nov. 4, 2022, in 9 pages.

Japanese Patent Office, Office Action, Application No. dated JP2019-033609, dated Jan. 31, 2013, in 3 pages.

* cited by examiner

EAR THERMOMETER

CROSS REFERENCE TO RELATED APPLICATIONS

This application is a Bypass Continuation of International Application No. PCT/JP2020/006654, filed on Feb. 20, 2020, and based upon and claims the benefit of priority from Japanese Patent Application No. 2019-033609, filed on Feb. 27, 2019, the entire contents of all of which are incorporated herein by reference.

TECHNICAL FIELD

The disclosure relates to an ear thermometer for measuring a body temperature of a temperature measurement target person.

BACKGROUND

For example, in an operating room, an intensive care unit, or the like, it is essential to measure a body temperature of a temperature measurement target person during the operation.

Further, for example, it may be necessary to measure a body temperature as a part of physical condition management for workers who work for a long period of time with a large physical burden and athletes who play various sports.

Since it is necessary to continuously measure a body temperature of a temperature measurement target person such as a patient, a worker, or an athlete over a long period of time, it is important to reduce the burden on the body.

As a conventional thermometer responding to such demands, an ear thermometer has been proposed which measures the temperature of an eardrum by inserting a probe into the ear hole of a temperature measurement target person (see JP 5039618 B2).

SUMMARY

The ear thermometer measures a body temperature by detecting infrared rays emitted from an eardrum with an infrared sensor.

However, in the conventional ear thermometer, since a temperature of the eardrum is measured by one infrared sensor, there is a possibility that an error easily occurs between the actual body temperature and the measurement result.

The present application has been made in view of the above problems, and an object of the present application is to provide an ear thermometer capable of suppressing measurement errors.

In order to achieve the above object, an ear thermometer according to an embodiment includes a probe including an infrared sensor unit configured to measure a temperature of an eardrum of an ear of a temperature measurement target person in a non-contact manner, the probe configured to be attached to an ear hole of the temperature measurement target person. The probe includes a probe body configured to be inserted into the ear hole of the temperature measurement target person, a housing for supporting the probe body; and an in-ear type earpiece attached to the probe body and configured to abut on an inside of the ear hole of the temperature measurement target person. The infrared sensor unit includes a first sensor and a second sensor arranged in the probe body and spaced apart by a predetermined distance along a direction substantially orthogonal to the eardrum when the probe body is inserted into the ear hole of the temperature measurement target person.

Thus, the ear thermometer according to the embodiment can measure the body temperature more accurately by suppressing the measurement error.

The first sensor may be disposed in a recess formed in a tip side of the probe body and may be disposed at a focal point of a concave surface formed on a bottom side of the recess. The second sensor may be disposed below the concave surface.

Thus, the ear thermometer according to the embodiment can measure the body temperature more accurately.

The first sensor and the second sensor may be disposed on a sensor substrate, and the sensor substrate may be housed in the probe body and the housing.

Thus, the ear thermometer according to the embodiment can suppress the measurement error.

Each of the first sensor and the second sensor may be constituted of a thermistor temperature element.

Thus, the ear thermometer according to the embodiment can suppress the measurement error.

The ear thermometer according to the embodiment may further include: a first linearizer for linearizing the first temperature data acquired by the first sensor; a second linearizer for linearizing the second temperature data acquired by the second sensor; a radiation temperature convertor for calculating a radiation temperature by inputting a value obtained by the first linearizer into a predetermined conversion formula; and a body temperature convertor for calculating the body temperature by adding the radiation temperature to the value obtained by the second linearizer.

Thus, the ear thermometer according to the embodiment can measure the body temperature more accurately by suppressing the measurement error.

According to the embodiment, it is possible to provide an ear thermometer capable of suppressing measurement errors.

DETAILED DESCRIPTION

An ear thermometer E1 according to an embodiment will be described with reference to FIGS. 1 to 7.

Figure 1A:
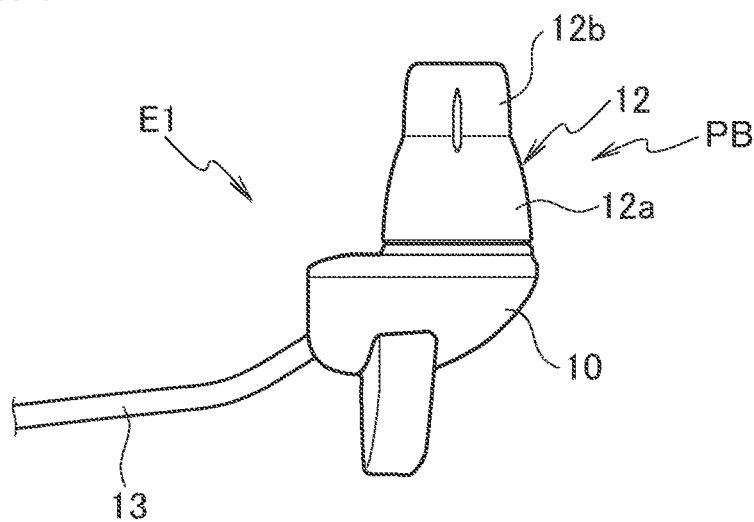
FIG. 1A is a right side view showing a configuration example of an ear thermometer according to an embodiment.
Figure 1B:
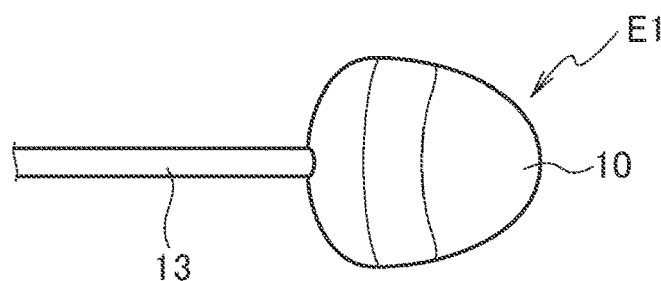
FIG. 1B is a bottom view thereof.
Figure 1C:
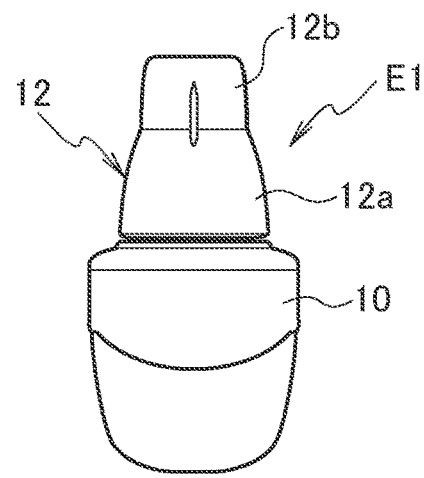
FIG. 1C is a front view thereof.
Figure 2:
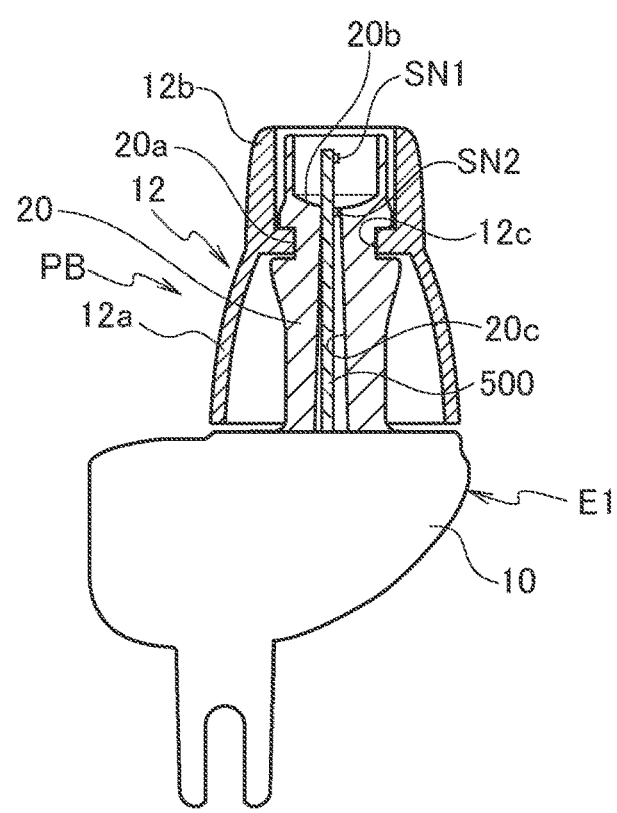
FIG. 2 is a partial sectional view showing a configuration example of an ear thermometer according to an embodiment.
Figure 3:
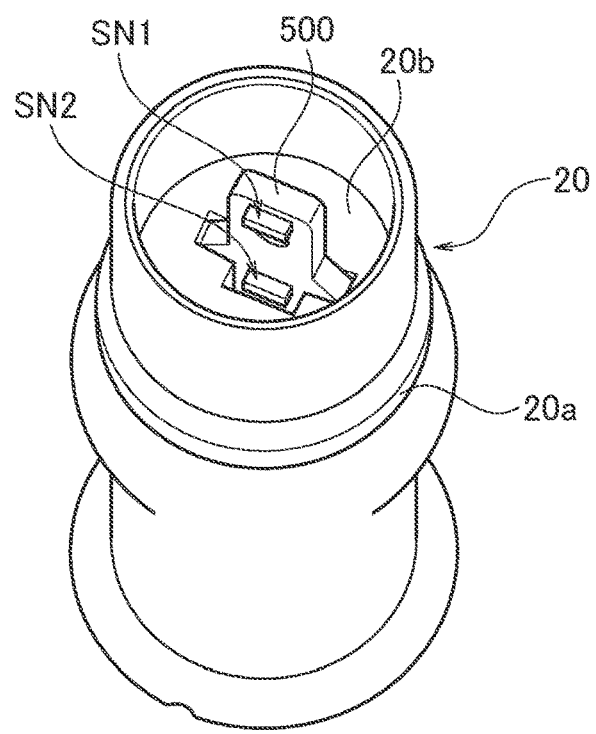
FIG. 3 is a perspective view of a principal portion of an ear thermometer according to an embodiment.
Figure 4:
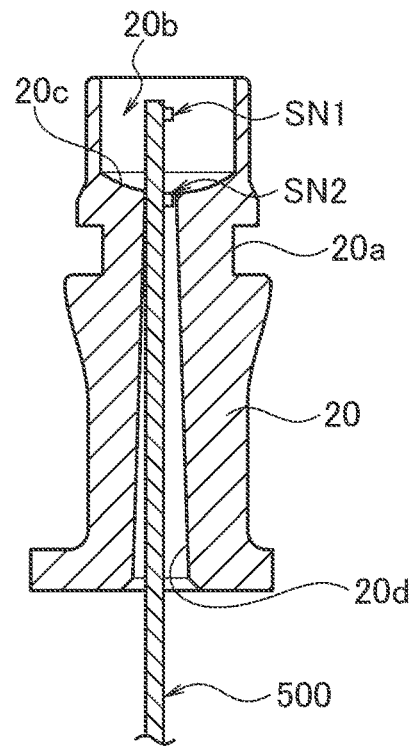
FIG. 4 is a cross-sectional view of a principal portion of an ear thermometer according to an embodiment.
Figure 5:
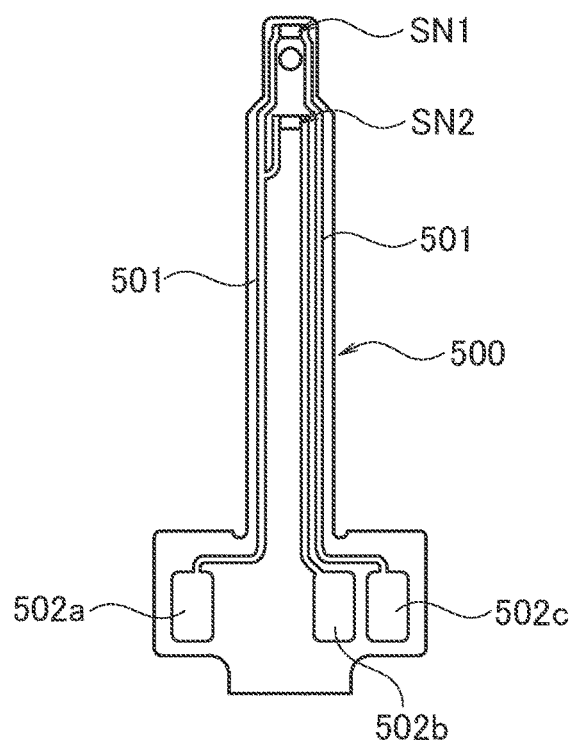
FIG. 5 is a plan view of a sensor substrate mounted on an ear thermometer according to an embodiment.

FIG. 1A is a right side view illustrating a configuration example of an ear thermometer E1 according to an embodiment, FIG. 1B is a bottom view of the same, and FIG. 1C is a front view of the same. FIG. 2 is a partial sectional view illustrating a configuration example of the ear thermometer E1. FIG. 3 is a perspective view illustrating a main part of the ear thermometer E1. FIG. 4 is a sectional view illustrating the main part of the ear thermometer E1. FIG. 5 is a plan view illustrating a sensor substrate 500 mounted on the ear thermometer E1.

As illustrated in FIGS. 1 and 2, the ear thermometer E1 according to the embodiment has a first sensor SN1 and a second sensor SN2 serving as an infrared sensor unit for noncontact measurement of the temperature of an eardrum of an ear of a temperature measurement target person, and a probe PB configured to be attached to the ear hole of the temperature measurement target person.

The probe PB includes a probe body 20 configured to be inserted into the ear hole of the temperature measurement target person, a housing 10 supporting the probe body 20, and an in-ear type earpiece 12 attached to the probe body 20 and configured to abut on the inside of the ear hole of the temperature measurement target person.

The housing 10 and the probe body 20 are formed of a synthetic resin such as ABS (Acrylonitrile-Butadiene-Styrene) resin. The housing 10 and the probe body 20 may be formed separately or integrally.

In the ear thermometer E1 according to the embodiment, the infrared sensor unit is arranged in a recess 20b formed on a tip side of the probe body 20.

The infrared sensor unit includes the first sensor SN1 and the second sensor SN2 arranged at a position close to an eardrum (not illustrated), and more accurate body temperature measurement can be performed by the first sensor SN1 and the second sensor SN2. A detailed configuration example of the infrared sensor unit will be described later.

As illustrated in FIG. 2 and the like, the earpiece 12 includes an engaging portion 12c engaging with a groove 20a on the probe body 20, a base portion 12a having a hollow conical shape in a part, and a substantially cylindrical shaped tip portion 12b extending in a direction away from the housing 10 at one end of the base portion 12a.

The base portion 12a and the tip portion 12b are integrally formed of a flexible material such as silicone rubber.

(Configuration of Infrared Sensor Unit)

As illustrated in FIG. 2 and the like, the infrared sensor unit includes the first sensor SN1 and the second sensor SN2 which are arranged in the probe body 20 and are separated by a predetermined distance along a direction substantially orthogonal to the eardrum when the probe body 20 is inserted into the ear hole of the temperature measurement target person.

The infrared sensor unit measures the temperature of the object (eardrum) by catching the temperature rise by infrared rays as a temperature difference (relative temperature) from the object (eardrum) to be measured and adding the temperature of the infrared sensor unit itself.

Each of the first sensor SN1 and the second sensor SN2 may be formed of a thermistor temperature element or the like.

As illustrated in FIGS. 2 to 4, the first sensor SN1 is arranged in the recess 20b formed on the tip side of the probe body 20 at the focal point of a concave surface 20c formed on the bottom side of the recess 20b.

Thus, the first sensor SN1 can efficiently receive infrared rays incident from the front of the sensor.

Since the first sensor SN1 is disposed at the focal point of infrared rays reflected from the concave surface 20c behind the first sensor SN1, the first sensor SN1 can receive infrared rays more efficiently.

The concave surface 20c may have a shape for condensing infrared rays from an assumed eardrum position (for example, about 10 mm forward).

As a result, the temperature of the first sensor SN1 receives infrared rays from the front and the concave surface 20c and rises higher than the space temperature where the first sensor SN1 is installed.

On the other hand, the second sensor SN2 is disposed below the concave surface 20c.

In this way, the second sensor SN2 is arranged at a position where infrared rays from the front surface and the concave surface 20c are not received as much as possible.

That is, by setting the second sensor SN2 to a position deeper than the concave surface 20c, a difference is generated between the infrared absorption amount of the first sensor SN1 and the infrared absorption amount of the second sensor SN2.

The second sensor SN2 absorbs a little infrared rays from the front, but by arranging the second sensor SN2 at a position deeper than the concave surface 20c, it is possible to obtain a space temperature that is a temperature at a time when the first sensor SN1 is not affected by infrared rays. The space temperature may also be referred to as a probe temperature.

The probe temperature is determined by a balance between heat flowing from the ear canal with which the probe is in contact and heat dissipating to the outside air from the probe back when the ear canal temperature is higher than the outside air temperature. When the ear canal temperature is lower than the outside air temperature, the heat flow is reversed.

As illustrated in FIG. 5, the first sensor SN1 and the second sensor SN2 are disposed on the sensor substrate 500.

The sensor substrate 500 is provided with terminals 502a, 502b, 502c, and a wiring 501 for connecting the terminals 502a, 502b, 502c, the first sensor SN1, and the second sensor SN2.

As illustrated in FIG. 4, the sensor substrate 500 is housed in a space 20d formed in the center of the probe body 20 and in the housing 10.

(Functional Structure of Ear Thermometer)

A functional configuration of the ear thermometer E1 according to the embodiment will be described with reference to a block diagram of FIG. 6.

Figure 6:
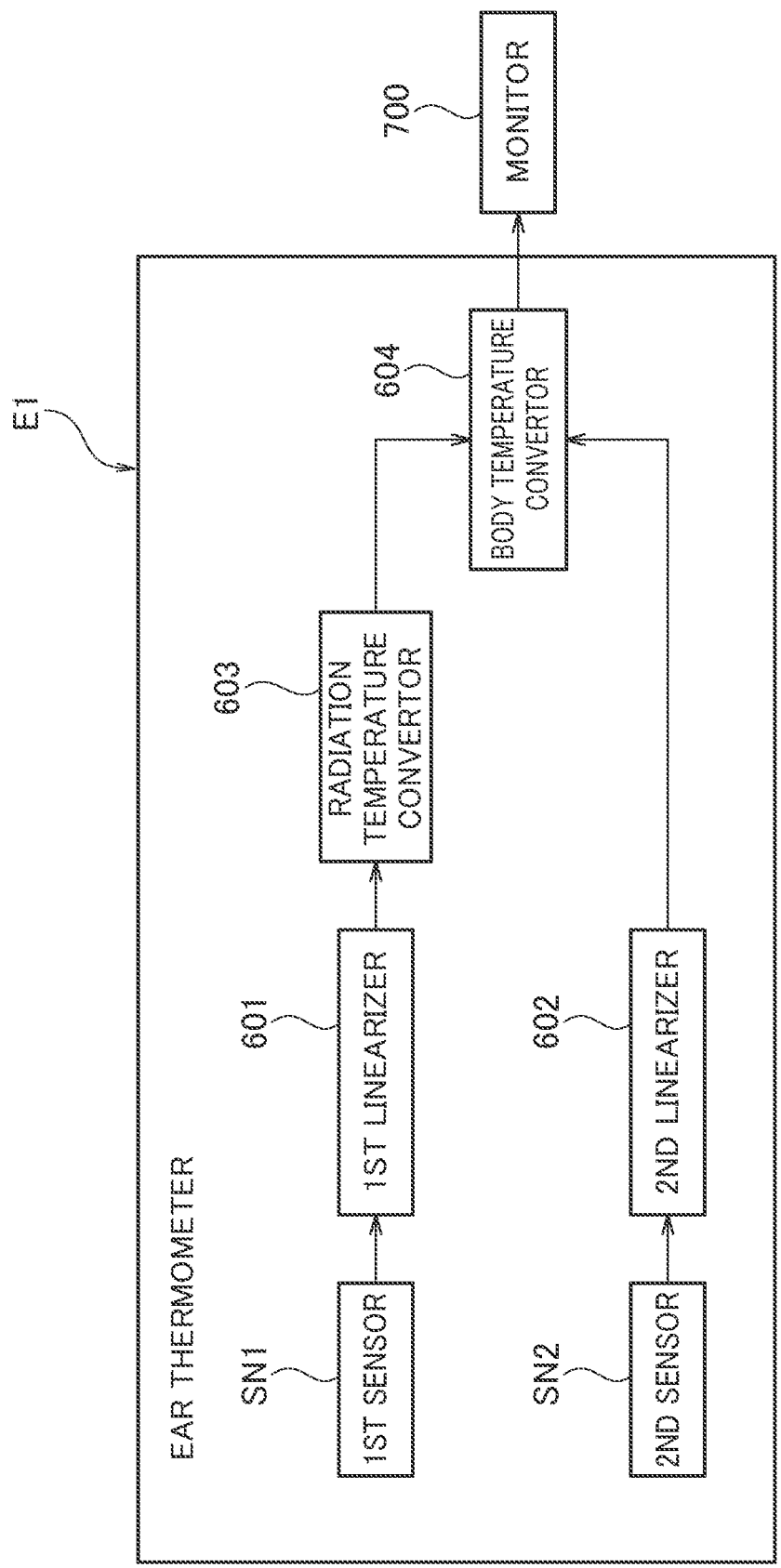
FIG. 6 is a block diagram showing the functional configuration of an ear thermometer according to an embodiment.

As illustrated in FIG. 6, the ear thermometer E1 includes the first sensor SN1, a first linearizer 601 for linearizing the first temperature data acquired by the first sensor SN1, the second sensor SN2, a second linearizer 602 for linearizing the second temperature data acquired by the second sensor SN2, a radiation temperature convertor 603 for calculating the radiation temperature by inputting the value obtained by the first linearizer 601 into a predetermined conversion formula, and a body temperature convertor 604 for calculating the body temperature by adding the radiation temperature to the value obtained by the second linearizer 602.

The first linearizer 601, the second linearizer 602, the radiation temperature convertor 603, and the body temperature convertor 604 are constituted by a microcomputer or the like.

An external device of the ear thermometer E1 is provided with a display 700 constituted of a liquid crystal display device or the like for displaying the body temperature calculated by the body temperature convertor 604.

The first linearizer 601, the second linearizer 602, the radiation temperature convertor 603, and the body temperature convertor 604 may constitute the external device with the display 700.

(Body Temperature Calculation Process)

Figure 7:
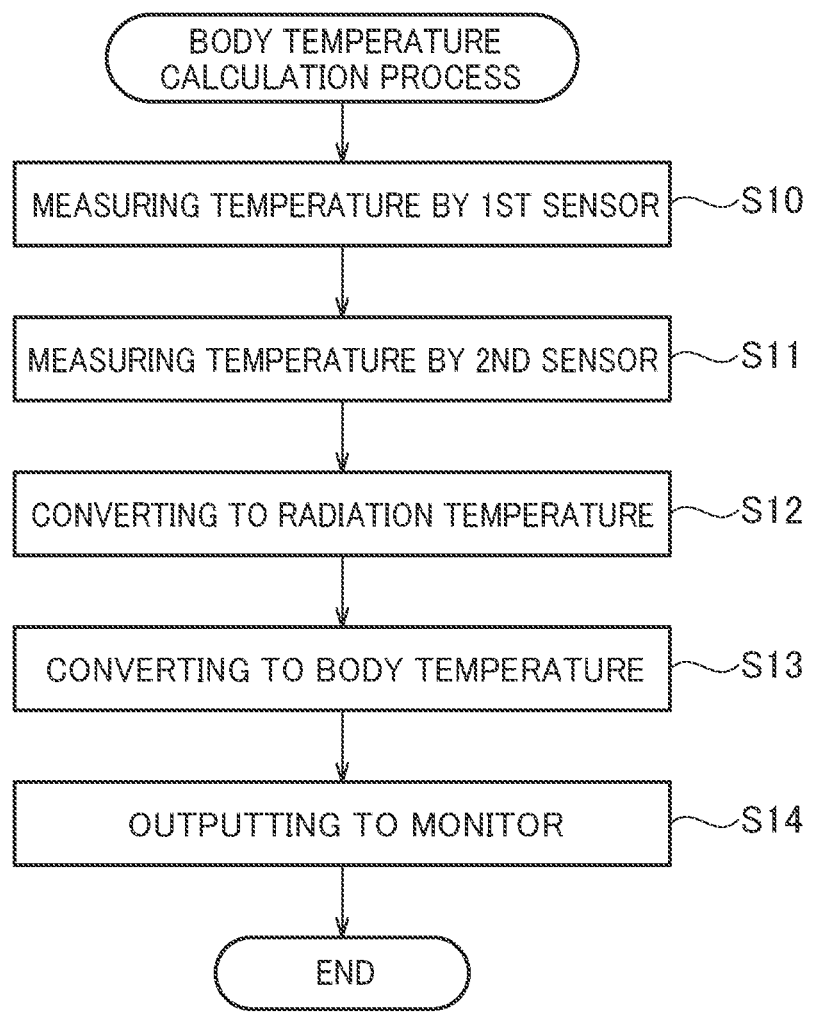
FIG. 7 is a flowchart showing a processing procedure of a temperature calculation process performed by an ear thermometer according to an embodiment.

Referring to the flowchart of FIG. 7, processing procedure of body temperature calculation process executed by the ear thermometer E1 according to the embodiment will be described.

First, in step S10, temperature measurement is performed by the first sensor SN1, and the measurement value is linearized by the first linearizer 601, and the process proceeds to step S11.

In step S11, the temperature measurement is performed by the second sensor SN2, and the measurement value is linearized by the second linearizer 602, and the process proceeds to step S12.

In step S12, the radiation temperature convertor 603 inputs the value obtained by the first linearizer 601 into a predetermined conversion formula to calculate the radiation temperature, and the process proceeds to step S13.

In step S13, the body temperature convertor 604 adds the radiation temperature to the value obtained in the second linearizer 602 to calculate the body temperature, and the process proceeds to step S14.

In step S14, the calculated body temperature is displayed on the display 700, and the processing is terminated.

Although the ear thermometer according to the present invention has been described above with reference to the illustrated embodiment, the present invention is not limited to this, and the constitution of each part can be replaced with an arbitrary constitution having a similar function.

What is claimed is:

1. An ear thermometer, comprising:
   a probe attached to an ear hole of a temperature measurement target person and comprising:
      an infrared sensor unit measuring a temperature of an eardrum of an ear of the temperature measurement target person in a non-contact manner, the probe
      a probe body inserted into the ear hole of the temperature measurement target person;
      a housing for supporting the probe body; and
      an in-ear type earpiece attached to the probe body and abutted on an inside of the ear hole of the temperature measurement target person,
   the infrared sensor unit comprising a first sensor and a second sensor arranged in the probe body and spaced apart by a predetermined distance along a direction substantially orthogonal to the eardrum when the probe body is inserted into the ear hole of the temperature measurement target person;
   a first linearizer for linearizing first temperature data acquired by the first sensor;
   a second linearizer for linearizing the second temperature data acquired by the second sensor;
   a radiation temperature convertor for calculating a radiation temperature by inputting a value obtained by the first linearizer into a predetermined conversion formula; and
   a body temperature convertor for calculating the body temperature by adding the radiation temperature to the value obtained by the second linearizer.

2. The ear thermometer of claim 1, wherein
   the first sensor is disposed in a recess formed in a tip side of the probe body and is disposed at a focal point of a concave surface formed on a bottom side of the recess; and
   the second sensor is disposed below the concave surface.

3. The ear thermometer of claim 1, wherein
   the first sensor and the second sensor are disposed on a sensor substrate, and
   the sensor substrate is housed in the probe body and the housing.

4. The ear thermometer of claim 1, wherein
   each of the first sensor and the second sensor is constituted of a thermistor temperature element.

* * * * *